United States Patent [19]

Refojo et al.

[11] 4,300,557
[45] Nov. 17, 1981

[54] METHOD FOR TREATING INTRAOCULAR MALIGNANCIES

[75] Inventors: Miguel F. Refojo, Boston; Hsaio S. Liu, Arlington, both of Mass.

[73] Assignee: The United States of America as represented by the Secretary of the Department of Health and Human Services, Washington, D.C.

[21] Appl. No.: 110,045

[22] Filed: Jan. 7, 1980

[51] Int. Cl.³ .............................................. A61M 7/00
[52] U.S. Cl. ..................................... 128/260; 128/1.1
[58] Field of Search .................. 128/1 R, 1.1, 1.2, 260

[56] References Cited

U.S. PATENT DOCUMENTS 3,872,856  3/1975  Clayton ................................ 128/1.2
4,201,210  5/1980  Hughes et al. ....................... 128/260

OTHER PUBLICATIONS

Refojo et al., J. of Bioengineering, vol. 2 (1978), p. 437.
Liu et al., Invest. Ophthalmol. Visual Sci., vol. 18 (1979), p. 1061.
Schmidt et al., Trans. Amer. Soc. Artif. Int. Organs., vol. XVIII (1972), p. 45.

Rosenblum et al., Cancer Research, vol. 33 (1973), p. 905.

*Primary Examiner*—C. Fred Rosenbaum
*Attorney, Agent, or Firm*—John S. Roberts, Jr.

[57] ABSTRACT

An improved process for dispensing a lipid soluble labile drug, i.e. 1,3-bis-(2-chloroethyl)-1-nitrosourea (BCNU) by diffusion through a silicone capsule implanted at a periocular site to an intraocular site within an animal body being treated with the drug, the improvements wherein the silicone capsule is provided with a tube sealed at the distal end thereof and provided with longitudinal slit cut through the tube wall inside the capsule for filling the capsule following implantation of the capsule, wherein the capsule is implanted surgically near the site being treated so that the tube is accessible for filling without further surgical procedures and wherein the drug is injected into the capsule through the tube in the form of a solution in a solvent which is non-toxic to the animal being treated, inert with respect to the drug dissolved therein and capable of diffusing from the capsule within 5 hours to leave a residue of the drug in the capsule.

7 Claims, 6 Drawing Figures

METHOD FOR TREATING INTRAOCULAR MALIGNANCIES

The invention described herein was made in the course of work under a grant or award from the Department of Health, Education and Welfare.

BACKGROUND OF THE INVENTION

This invention relates to an improved method of dispensing a highly cytotoxic lipid-soluble, labile drug, such as 1,3-bis-(2-chloroethyl)-1-nitrosourea (BCNU) to a limited area of an animal body being treated therewith.

PRIOR ART STATEMENT

Treatment of intraocular or other malignancies limited to an area of an animal body with anti-cancer drugs is recognized as a useful supplement to conventional therapy. However, systemic administration of typical anti-cancer drugs generally has one or more undesired side effects, including depression of hematapoiesis and/or renal or hepatic toxicity. These side effects obviously limit the safe dosage of anti-cancer drugs and unduly prolong the course of therapy. Such complications could be prevented by sustained administration of an anti-cancer drug directly to the site of the tumor from an implanted device, so as to achieve a high drug concentration only at the tumor site and a significantly reduction of systemic toxicity.

Sustained delivery at the tumor site is particularly beneficial for patients whose physical condition will not tolerate radiation therapy or systemic administration of cytotoxic drugs in large amounts or whose tumors are in an early stage in which accurate diagnosis is impossible. Administration of cytotoxic drugs directly to the affected area is particularly important in the case of intraocular malignancies, particularly when the patient being treated refuses enucleation.

BCNU (NSC 409,962) is effective against a variety of tumors in animal and man. It is a yellowish, low melting solid which degrades rapidly in aqueous media. The drug is consequently labile in the presence of moisture, particularly at body temperature. Administration of the drug to a tumor site from an implanted source thereof has not yet been accomplished satisfactorily. Accordingly, the development of alternative methods for sustained administration of BCNU and related cytotoxic drugs is of continuing interest.

The release of BCNU from refillable silicone rubber implants for the treatment of intraocular malignancies has been reported by Refojo et al., *J of Bioengineering*, Vol. 2 (1978), at 437 (published Jan. 10, 1979), incorporated herein by reference. Studies on sustained release of BCNU for treating intraocular malignancies in animals has been reported by Liu et al, *Invest. Ophthalmol. Visual Sci.*, Vol. 18 (1979) at 1061, incorporated herein by reference.

Liu et al. have also studied delivery of BCNU by direct injection into the subconjunctival space or anterior chamber, with or without supplemental intravenous administration of BCNU as a therapy for intraocular malignancy (Brown-Pearce epithelioma), report in *Invest. Ophthalmol. Visual Sci.*, Vol. 17 (1978), at 993.

Schmidt et al, *Trans Ameri Soc. Artif. Int. Organs.* Vol. XVIII (1972) at 45, have described diffusion of nitrosourea cancer chemotherapeutic agents through implanted silicone rubber capsules for treatment of mice carrying L 1210 leukemic cells. Sesame oil, which diffuses from the capsules more slowly than ethanol, was preferred to ethanol as solvent for BCNU.

Rosenblum et al., *Cancer Research*, Vol. 33 (1973) at 905, report similar studies with dry crystalline 1-(2-chloroethyl)-3-(trans-4-methylcyclohexyl)-1-nitrosourea (methyl-CCNU) encapsulated in silicone rubber.

Administration of anti-tumor agents including nitrosoureas, from silicone rubber devices impregnated therewith, subcutaneously to L 1210 leukemic mice has been reported by Neil et al., *Chemotherapy*, Vol. 18 (1973), at 27.

Arlen, in U.S. Pat. No. 3,765,414, has proposed a drug release system, relying on transport of active agent through a hydrophilic membrane, in which a given therapeutic agent can be replaced by another.

Zaffaroni et al have proposed in U.S. Pat. No. 4,036,227, a device for releasing a drug to a limited area of an animal body, in which bioerosion of a material covering the device controls the rate at which the drug is administered.

The use of expandable silicone implants for scleral buckling has been disclosed by Banuelos et al., *Arch. Ophthalmol.* Fol 89 (1973), at 500. Expansion of an intravitreous silicone balloon by saline solution has been proposed to treat otherwise inoperable cases of retinal detachment by Tolention et al., *Ophthalmic Surgery*, Vol. 9 (1978), at 73. Further disclosures on expandable silicone implants, including relase of antibiotics therefrom, were made by Refojo et al., *Arch. Ophthalmol.*, Vol 9 (1973), at 127 and Huamonte et al., ibid, Vol. 93 (1975) at 354 and 429. Sustained release of antibiotics from other materials used for scleral buckling procedures has been studied by Refojo et al., *Ophthalmol. Res.*, Vol. 7 (1975) at 33 and Refojo, ibid at 459.

SUMMARY OF THE INVENTION

This invention relates to an improved process for dispensing a lipid-soluble, labile drug by diffusion through an implantable silicone capsule to a site within an animal body being treated with the drug, wherein the silicone capsule is provided with a tube sealed at the distal end thereof and through the interior wall of which is cut a longitudinal slit of 1–1.5 mm. for filling the capsule following implantation of the capsule, wherein the capsule is implanted surgically near the site being treated so that the tube is accessible for filling without further surgical procedures and wherein the drug is injected into the capsule through the tube in the form of a solution in a solvent which is non-toxic to the animal being treated, inert with respect to the drug dissolved therein and capable of diffusing from the capsule within 5 hours to leave a residue of the drug in the capsule.

In another aspect this invention relates to a process of dispensing a drug selected from the group consisting of BCNU, CCNU and methyl-CCNU through an expandable, silicone microballoon implanted periocularly to an intraocular site within an animal body at a constant rate wherein the drug is placed within the balloon in the form of a solution of a rapidly diffusible solvent and is dispensed by diffusion through the silicone owing to lipophilic properties.

BRIEF DESCRIPTION OF THE DRAWINGS

FIG. 1, including

DETAILED DESCRIPTION

Silicone rubbers which can be used to fabricate the permeable implants used in the practice of this invention are selected from medical grade silicones, as discussed by Braley, "The chemistry and properties of medical grade silicone" in "Biomedical Polymers," Rembaum et al., editors, New York, Marcel Dekker, Inc. (1971) at 35–50. Typical of the materials which can be used is Silastic 500-1 (Dow Corning), which contains silica filler to increase tensile strength. The implants are made from thin sheets of the silicone, of the order of 0.1–0.2 mm in thickness, so as to provide a strong balloon which nevertheless is thin enough to permit diffusion of BCNU or other active agents or diluents therethrough. The implantable balloons are translucent prior to being filled, but become transparent when filled.

The balloons are glued together at the edges with a silicone adhesive and contain a tube, sealed at the distal end with a compatible silicone sealant in the proximal end of which is cut a longitudinal slit.

1,3-Bis(2-chloroethyl)-1-nitrosourea (BCNU) can be prepared, for example, as disclosed by Yanko et al. in U.S. Pat. No. 4,028,410. Contemplated equivalents of BCNU include, but are not limited to, 1-(2-chloroethyl)-3-cyclohexyl-1-nitrosourea (CCNU) and 1-(2-chloroethyl)-3-(trans-4-methylcyclohexyl)-1-nitrosourea (methyl-CCNU).

Decomposition of BCNU in water and 1% ethanol solution is of the order of 140–305 minutes and 246 minutes respectively. Accordingly, these solvents for BCNU were initially considered unacceptable for long-term release of BCNU to the eye.

It was found that BCNU in dilute ethanol solution diffused from the silicone balloons into water at a rapidly decreasing rate, regardless of whether 1% or 10% ethanol was used as solvent for BCNU. This is shown by the dotted line in FIG. 2.

Figure 2:
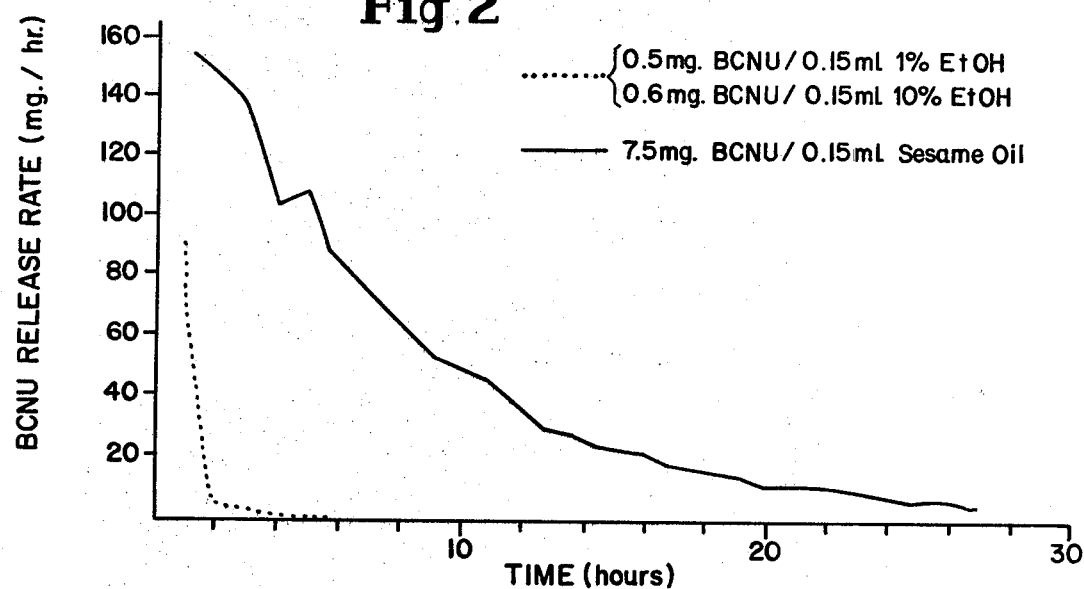
In FIG. 2 is shown the rate of release of 1,3-bis(2-chloroethyl)-1-nitrosourea (BCNU), dissolved in aqueous ethanol or sesame oil, from a silicone microballoon into water.

Sesame oil, in which BCNU is relatively stable and fairly soluble, was evaluated as a vehicle. It was found, as shown in FIG. 2, that silicone microballoons containing BCNU in sesame oil released BCNU into water at a variable rate and that the BCNU was depleted rather rapidly.

Figure 3:
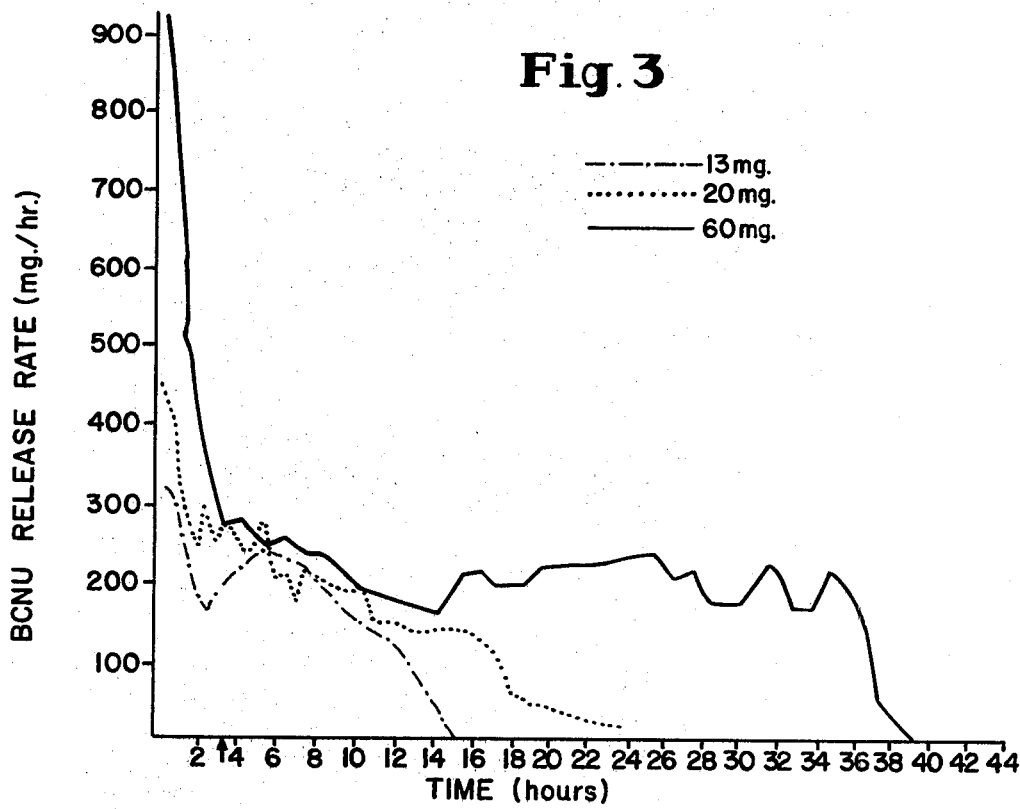
FIG. 3 represents the rate of BCNU release from absolute ethanol solution.

Experiments using BCNU in absolute ethanol, which is an excellent solvent for BCNU, showed that the alcohol diffused through the silicone microballoon rapidly, within 3–4 hours, to leave a residue of solid BCNU in the balloon. Thereafter, as shown in FIG. 3, BCNU diffused from the balloon into water at a relatively constant rate.

Accordingly, absolute ethanol is preferred for the purposes of this invention. It will be understood that solvents which diffuse through silicone elastomers rapidly (within 5 hours), which are inert to BCNU or other active agents being administered and which are non-toxic to the substrate being treated are contemplated equivalents of ethanol and can be substituted therefor.

In vitro experiments with ethanolic solutions of BCNU in silicone microballoons implanted in agar cultures of $E.\ coli$ showed that the inhibitory activity of BCNU, whether owing to BCNU per se or its decomposition products, was unimpaired in comparison to results of similar assays using filter paper impregnated with known amounts of BCNU.

Consistent with results obtained in studies of BCNU diffusion from ethanolic solutions through silicone microballoons into water, studies of BCNU diffusion into agar culture of $E.\ coli$ suggest that all balloons contain essentially 100% BCNU after the first night's incubation. Diffusion rates were therefore similar for all balloons regardless of BCNU content and the length of activity is roughly a linear function of BCNU content, at least until BCNU decomposition becomes significant. In any event, the experiments in which 30 or 40 mg. of BCNU in ethanol are charged into silicone microballoons inhibit growth of $E.\ coli$ cultures for 6 days.

In accordance with this invention, it is feasible to implant a silicone microballoon in the eye or other organ being treated, with the tube remaining accessible, and fill the balloon with BCNU solution or other active agent at intervals of several days. It will be appreciated that this procedure permits administration of highly labile cytotoxic agents to limited areas of the body over extended periods of time without requiring repeated surgical procedures.

In vivo testing of this drug delivery concept was carried out in New Zealand female albino rabbits with normal eyes inoculated intercamerally with Brown-Pearce epithelioma tissue. Three days thereafter, silicone microballoons were implanted episclerally in each eye. BCNU solution was injected into the balloon. In each animal, the fellow eye served as control and received diluent only. The greatest reduction in tumor growth was observed using 0.13 mg of BCNU in 15 ml. of absolute ethanol, injected on days 3 and 6. Significant reduction of tumor growth was achieved using 3.0 or 12.0 mg of BCNU in 0.15 ml. of sesame oil, injected on days 3, 6 and 9.

The good therapeutic results obtained with BCNU solutions in absolute ethanol using silicone balloons 0.1–0.2 mm in wall thickness, is quite unexpected in view of Schmidt et al., supra which recognized that ethanol diffused rapidly through silicone rubber, purportedly with crystallization of BCNU on the inner surface of the capsule to produce a decrease in surface area available for diffusion and to account for rapid decrease in BCNU concentration in the dialysate being monitored. Results in accordance with the present invention, showing similar drug depletion rates in microbiological assays comparing BCNU (solid) in a sandwiched silicone device with BCNU in absolute ethanol in a microballoon device, are also unexpected in view of Schmidt et al.

DESCRIPTION OF MOST PREFERRED EMBODIMENT

In a most preferred embodiment, the process of this invention is as above, wherein the site being treated is the eye, the drug being administered is 1,3-bis(2-chloroethyl)-1-nitrosourea and the solvent is absolute ethanol by volume.

In the following examples, the temperatures are set forth uncorrected in degrees Celsius. Unless otherwise indicated, all parts and percentages are by weight.

EXAMPLE 1

Preparation of Expandable Silicone Rubber Implanted Balloons

The balloons were made from two sheets of silicone rubber (Silastic 500-1, Dow Corning, 0.1 mm thick). The sheets were glued at the edges (1 mm) with silicone adhesive (Dow Corning) to produce a balloon having an oblong cavity about 8×4 mm. in the center, into which a tube of silicone rubber 0.3 mm in diameter extended. The end of the silicone tubing was sealed with silicone adhesive, and a longitudinal slit (about 1 to 1.5 mm long) was cut through the wall of the tube before implantation so that the expandable implant retained injected fluid without the filling tube being tied.

Figure 1A:
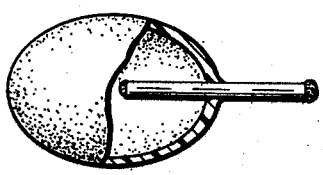
FIGS. 1A and 1B, represents the structure of the implantable silicone microballoon used in the practice of the invention.

A top view of an implant thus prepared is given in FIG. 1A.

Figure 1B:
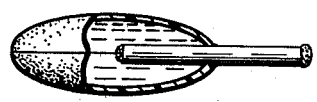

The balloons, filled with about 0.15–0.2 ml. of solution, expanded according to a side view given in FIG. 1B.

EXAMPLE 2

Stability of and analysis of BCNU in aqueous solution

The decomposition of BCNU in water and in 1% aqueous ethanol was followed by measuring the characteristic BCNU absorbance maximum at 232 nm, using a Beckman DK-2A spectrophotometer. A second maximum that appeared at 190 nm and increased during decomposition was not a reliable indicator of the drug's breakdown. The half-life of BCNU in water at 37° C. was 230 minutes. The half-life of BCNU in 1% ethanol, at 37° C., was 246 minutes.

The reported half-life of BCNU in water is 305 minutes, Montgomery et al., *J. Med. Chem*, Vol. 10 (1967) at 668–674, or 140 minutes, Schmidt et al, supra.

EXAMPLE 3

(a) Release of BCNU dissolved in aqueous ethanol from silicone balloons into water Into one balloon prepared as in Example 1 was injected 0.15 ml. of 1% ethanol containing 0.6 mg. of BCNU and into a second balloon 0.15 ml. of 10% ethanol containing 0.5 mg of BCNU.

Each balloon was placed in a scintillation vial containing 5 ml of water and shaken at 37° C. in an automatic shaker. At specified time intervals, the aqueous liquid was removed from the vials containing the balloons. The amount of BCNU dissolved in the water was determined by spectroscopic analysis (absorbance at 232 nm). The water in each scintillation vessel was replaced with 5 ml. of fresh water. Shaking at 37° C. and replacement of the water in the vial was continued for additional time intervals, until the aqueous liquid removed from the vials did not absorb at 232 nm. Results for both ethanolic solutions were as in FIG. 2. (- - -).

(b) Release of BCNU in sesame oil solutions from silicone balloons into water

BCNU (7.5 mg/0.15 ml sesame oil) was injected into a silicone balloon which was placed in a flask with 5 ml of distilled water and shaken in an automatic shaker at 37° C. The procedure of Example 3(a) was repeated for as many time as positive absorption at 232 nm was recorded. When the experiment had to be interrupted overnight, the dried silicone balloon containing BCNU in sesame oil was stored at −15° C. The results of this experiment are shown in FIG. 2 (—).

EXAMPLE 4

Release of BCNU in absolute ethanol from silicone balloons in water

BCNU in absolute ethanol solution (13 mg/0.15 ml, 20 mg/0.15 ml, and 60 mg/0.15 ml) was injected in each of three silicone balloons. Release of BCNU from the balloon was followed as in Example 3. Results of this experiment are shown in FIG. 3, in which (—. —. —.) represents data for the solution containing 13 mg of BCNU, (- - -) the solution containing 20 mg and (—) the solution containing 60 mg. A sharp drop in the BCNU release rate after 3–4 hours, indicated by the arrow in the Figure, is correlated with diffusion of all of the ETOH from the balloons. After alcohol depletion, essentially pure BCNU remained inside the balloons. Thereafter BCNU release rate was about the same for the three balloons until decomposition and diffusion had depleted the BCNU in the balloons. The balloon containing the largest amount of BCNU released it over the longest time.

EXAMPLE 5

(a) Microbiological assay of BCNU in ethanol solutions

BCNU activity was evaluated by placing a silicone balloon containing BCNU in 0.2 ml of ethanol in a gelled agar plate seeded with *E. coli* ($10^6$ colonies/ml). The balloon was covered with a layer of seeded agar. The culture was incubated overnight at 35° C. and the zone of inhibition was measured. The balloons were transferred daily to new plates and the procedure repeated as long as activity was detected. The diameters of the zones of inhibition were compared with a standard semilogarythmic plot obtained using known amount of BCNU absorbed in filter paper about the size of the balloons. As shown in Example 4, ethanol diffuses from the silicone balloons at a faster rate than does BCNU, so that after the first incubation in agar gels, essentially pure BCNU remains inside the balloons. In control experiments with balloons filled with 0.2 ml of ethanol no inhibition of *E. coli* was observed. After a single overnight incubation, all of the alcohol had diffused from the balloon.

Figure 4:
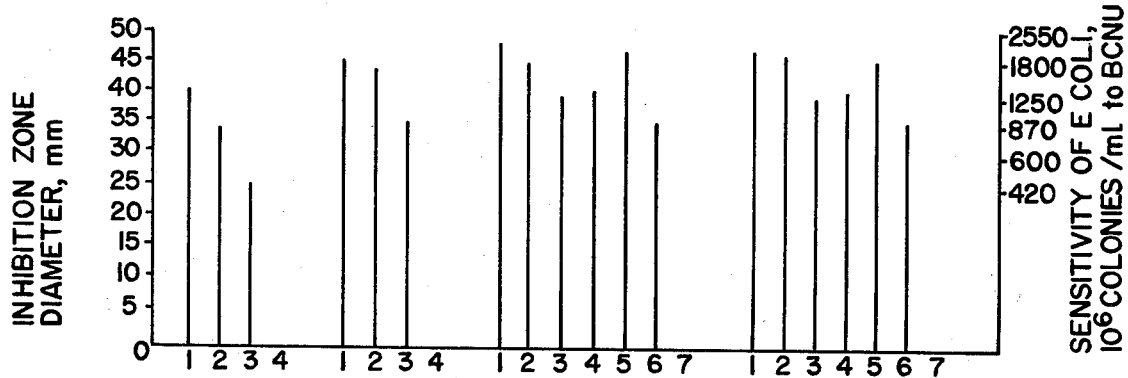
In FIG. 4 is shown inhibitory activity of BCNU in absolute ethanol in silicone microballoons, embedded in agar cultures of E. Coli.

The incubated plates showed two concentric and distinct zones of inhibition, possibly caused by degradation of BCNU. The smaller zone was very clear, and probably totally free of bacterial growth. The larger one was distinct, but had some diffuse bacterial growth. Although the diameter of both concentric zones was recorded, FIG. 4 shows only the larger diameters for runs with balloons containing 10, 20, 30 and 40 mg. of BCNU in 0.2 ml. of ethanol. The microbiological assay is a useful test of cytotoxic activity of the implants, but the results are only semiquantitative, owing to simultaneous decomposition and diffusion of BCNU.

The results of *E. coli* inhibition in agar plates obtained with different amounts of BCNU in ethanol solution in the balloons are similar to each other, since after the first overnight incubation all the balloons contain essentially 100% BCNU. Diffusion rates should be similar for all the balloons regardless of the amount of BCNU contained, but higher BCNU content in the balloon should produce a longer period of activity. However, results with balloons containing 30 and 40 mg., respectively, of BCNU were essentially the same: comparable activity for six consecutive incubations, and zero activity for the seventh. Lack of activity in the seventh incubation is probably due to total decomposition of the drug rather than to depletion by diffusion. Accordingly, the factor limiting prolonged delivery of BCNU from silicone balloons may be decomposition within the balloons under physiological conditions.

(b) Microbiological assay of solid BCNU

A 10 mg sample of solid was placed in a 7-mm-diameter reservoir made of two silicone membranes (0.1 mm thick) separated by a silicone rubber ring spacer (1.0 mm wide × 1.5 mm thick) and glued with silicone adhesive. The sandwich-type silicone device containing 10 mg of solid BCNU was imbedded in agar plates seeded with *E. coli* and incubated repeatedly as in Example 5(a). The results of this assay showed depletion of drug activity similar to that obtained with 10 mg BCNU in 0.2 ml ethanol in a silicone balloon.

EXAMPLE 6

In vivo testing in rabbits

Preoperative examination of 28 eyes in 14 New Zealand femal albino rabbits weighing 2.0 to 2.5 kg included biomicroscopy, tonotometry, and indirect ophthalmoscopy. All animals had normal eyes. Both eyes of each animal were inoculated intracamerally with Brown-Pearce epithelioma tissue by the technique at 993 of Liu et al., *Invest. Ophthalmol Visual Sci.*, Vol. 17 (1978).

Figure 5:
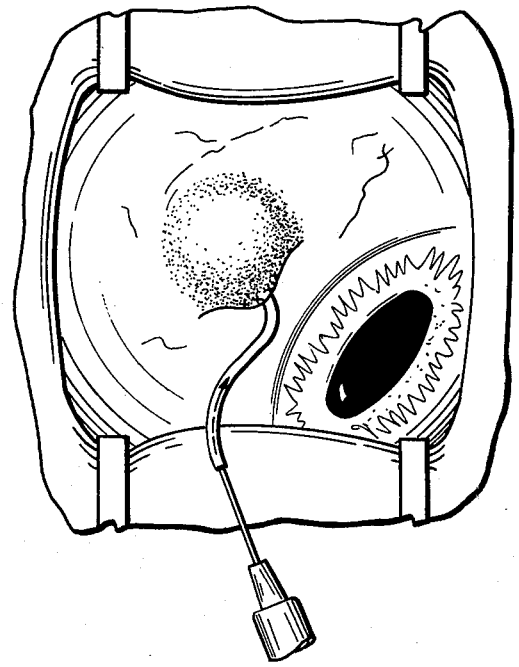
In FIG. 5 is shown a microballoon implanted near the eye of a rabbit.

Three days after tumor tissue implantation, a silicone device described in Example 1 was implanted episclerally in each eye. Animals were anesthetized with sodium pentobarbital 24 mg/kg body weight administered intravenously. After routine preparation of the rabbit and the eyes, a pocket beneath the conjunctiva and Tenon's capsule was made in the upper temporal quadrant of the eye. The silicone device was inserted into the pocket but the small tube remained accessible to permit injection of test substance. Two 7-0 silk sutures were applied on both shoulders of the silicone device and on the episcleral tissue at the pars plana to hold the device in position. The conjunctiva was closed with two 7-0 silk sutures. Then 0.15 ml of the BCNU solution or the diluent (control) was injected into the device with a tuberculin syringe and a 30-gauge needle through the tube which was outside the closed conjunctiva as shown in FIG. 5. The injecting tube was fixed on the upper fornix.

Seven animals (Group 1A) received 3.0 mg of BCNU in 0.15 ml of sesame oil in one eye on the third, sixth, and ninth days after tumor implantation (total dose 9.0 mg). Three animals (Group 1B) received 12.0 mg of BCNU in 0.15 ml of sesame oil on the same schedule (total dose 36.0/mg). Four animals (Group II) received 13.0 mg of BCNU in pure ethanol on the third and sixth days after tumor implantation (total dose 26.0 mg). The fellow eyes served as controls and received diluent only.

Ocular examinations were made on alternate days during the 20 days following tumor implantation; at that time all eyes were enucleated. The effectiveness of treatment was measured by (1) comparing the extent of tumor growth in the anterior chamber of treated and control eyes, (2) noting the occurrence of distortion and perforation of the globe due to tumor growth, (3) weighing all eyes following enucleation, and (4) comparing the histopathologic changes in the eyes.

The enucleated eyes were fixed in 10% buffered formalin in preparation for histopathological examination. A sagittal section on either side of the optic nerve was made. Pupil-optic nerve sections and the two calottes were processed routinely for histologic evaluation, using hematoxyline and eosin (H&E) stain. The eyes were imbedded in paraffin and cut in sections 6μ thick for light microscopy. Every fifth section was stained. About 50 sections from each eye were examined.

Clinical results, tabulated below, indicate the day on which the tumor occupied the anterior chamber and the weight of the enucleated eyes. The first day was the day on which tumor tissue was implanted.

| Group | Day Tumor Occupied Anterior Chamber | | Day Tumor Destroyed Whole Eye | | | Weight of Eyes After Enucleation (g) | |
|---|---|---|---|---|---|---|---|
| | Treated Eye | Control Eye | Treated Eye | Control Eye | | Treated Eye | Control Eye |
| II | 18 | 10 | 20* | 14 | | 2.8 | 5.4 |
| | 15 | 11 | 20* | 15 | | 3.2 | 6.4 |
| | 20 | 12 | 20* | 16 | | 3.2 | 3.7 |
| | 20 | 12 | 29* | 14 | | 3.3 | 5.9 |
| | | | | | Aver. wt (Gr. II) | 3.1 | 5.41 |
| | | | | | Aver. wt. (all eyes) | 4.6 | 6.5 |
| IA | 14 | 9 | 18 | 13 | | 4.4 | 7.9 |
| | 18 | 10 | 18* | 11 | | 4.2 | 6.8 |
| | 12 | 10 | 15 | 12 | | 6.7 | 7.0 |
| | 13 | 10 | 18 | 13 | | 4.9 | 5.4 |
| | 14 | 10 | 19 | 13 | | 5.1 | 6.4 |
| | 12 | 10 | 17 | 11 | | 9.3 | 9.9 |
| | 12 | 10 | 16 | 14 | | 5.1 | 5.7 |
| B | 20 | 13 | 20* | 15 | | 3.5 | 9.2 |
| | 17 | 10 | 20 | 15 | | 3.5 | 6.3 |
| | 11 | 9 | 17 | 13 | | 5.2 | 5.5 |
| | | | | | Aver. wt (Gr. I) | 5.2 | 7.0 |
| | | | | | (Gr. IA) | 5.7 | |
| | | | | | (Gr. IB) | 4.1 | |

*Eye not yet destroyed by day of enucleation

CLINICAL RESULTS (a) Control eyes

In untreated eyes, the implanted epithelioma usually filled the anterior chamber within 10 to 12 days after tumor tissue implantation. Of the 14 control eyes, 13 were distorted and ruptured due to tumor expansion within 15 days. The last one was ruptured at 16 days. The average weight of the globe following enucleation was 6.5 gr; normal weight is 3.182 g±0.506.

(b) Group 1: Eyes treated with BCNU in sesame oil

Growth of the implanted tumor tissue in the anterior chamber was slowed in all 10 eyes. In six eyes of the seven that had received three doses of 3.0 mg of BCNU in sesame oil (Group 1A), retention of normal shape and size of the eye without distortion for 15 days following tumor implantation was evidence that tumor growth was slowed. Two eyes of the three that had received three doses of 12.0 mg of BCNU in sesame oil (Group 1B), retained their normal shape and size without distortion for 19 days following tumor implantation. The average weight of the 10 treated eyes after enucleation was 5.2 g.

(c) Group II: Eyes treated with BCNU in pure ethanol.

Each of the four eyes treated showed good response. On the fifteenth day following tumor implantation, tumor tissue growth in the anterior chamber was almost completely arrested in three of the four treated eyes. On the twentieth day after tumor implantation, all four treated eyes retained their normal shape and size. The average weight of the four treated eyes after enucleation was 3.1 gm; the average weight of the fellow control eyes was 5.4 gm.

HISTOPATHOLOGICAL OBSERVATIONS (a) Control eyes

Tumor often filled the globe and extended into the subconjunctival space or orbit so that the intraocular contents were completely infiltrated and replaced by tumor. The site of rupture of the globe resulting from tumor growth was usually anterior between the limbus and ora.

Two main cell types were noted in the tumor. Most cells were round to ovoid with ill-defined cell margins and scant eosinophilic cytoplasm, giving an epithelioid appearance. The nuclei were large with prominent nucleoli and chromatin clumping. Other cells tended to be spindle-shaped, but also had large nuclei and prominent nucleoli. Their cytoplasm was also ill-defined and they showed mild basophilia. Both types of cells showed marked mitotic activity (6 to 8 per high power field). The sclera and episcleral tissues were diffusely infiltrated by tumor cells.

(b) Group I: Eyes treated with BCNU in sesame oil

Tumor growth tended to be limited to the anterior segment, but in some instances replaced the iris and ciliary body. The inner scleral and corneal lamellae were infiltrated with tumor; no extrascleral extension was noted. The mitotic index remained high and necrosis was prominent. There was no observable difference histologically between Group IA eyes, which had received a total of 9.0 mg of BCNU, and Group IB eyes, which had received a total of 36.0 mg.

(c) Group II: Eyes treated with BCNU in pure ethanol.

These eyes exhibited the most significant reduction of tumor growth. Only small foci of tumor, limited to the anterior segment, were observed. Typically, small nodules of tumor were found in the iris stroma and iris root with occasional involvement of the ciliary body. The mitotic index was high, (6 to 8 per high power field) but necrosis was less prominent than in control eyes. Normal intraocular architecture was maintained, with no evidence of invasion of the cornea or sclera.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In the process of dispensing a lipid-soluble, labile drug by diffusion through an implantable silicone capsule to a site within an animal body being treated with the drug, the improvements wherein the silicone capsule is provided with a tube sealed at the distal end thereof and provided with a longitudinal slit cut through the tube wall inside the capsule for filling the capsule following implantation of the capsule, wherein the capsule is implanted surgically near the site being treated so that the tube is accessible for filling without further surgical procedures and wherein the drug is injected into the capsule through the tube in the form of a solution in a solvent which is non-toxic to the animal being treated, inert with respect to the drug dissolved therein and capable of diffusing from the capsule within 5 hours to leave a residue of the drug in the capsule.

2. The process of claim 1, wherein the capsule is subsequently refilled with one or more additional portions of the drug dissolved in the solvent.

3. The process of claim 1, wherein the site being treated is the eye, the drug being administered is 1,3-bis(2-chloroethyl)-1-nitrosourea and the solvent absolute ethanol.

4. The process of claim 1, wherein the capsule is in the form of a microballoon having walls 0.1–0.2 mm in thickness.

5. The process of claim 1, wherein the site being treated is the eye, the drug being administered is 1,3-bis(2-chloroethyl)-1-nitrosurea, the solvent is absolute ethanol, the capsule is in the form of a microballoon having walls 0.1–0.2 mm in thickness and the capsule is subsequently refilled with one or more additional portions of BCNU dissolved in absolute ethanol.

6. The process of claim 1 wherein the solvent is absolute ethanol.

7. The process of claim 1 wherein the microballoon has an average length of 8–10 mm, a width of 4–6 mm and walls of 0.1–0.2 mm.

* * * * *